United States Patent [19]

Pagani et al.

[11] 4,097,250
[45] Jun. 27, 1978

[54] METHOD FOR THE PURIFICATION OF NATURAL GAS HAVING A HIGH CONTENTS OF ACIDIC GASES

[75] Inventors: Giorgio Pagani, Milan; Gianfranco Guerreri; Bruno Peri, both of San Donato Milanese (Milan), all of Italy

[73] Assignee: Snamprogetti, S.p.A., Milan, Italy

[21] Appl. No.: 774,626

[22] Filed: Mar. 4, 1977

[30] Foreign Application Priority Data

Mar. 5, 1976 Italy ............................... 20900 A/76

[51] Int. Cl.$^2$ .............................................. B01D 19/00
[52] U.S. Cl. ........................................ 55/48; 55/49; 55/73; 62/27; 62/31; 62/34
[58] Field of Search ................... 55/48, 49, 68, 73; 62/17, 20, 24, 27, 31, 32, 34

[56] References Cited

U.S. PATENT DOCUMENTS 3,531,917 10/1970 Grunewald et al. .................... 55/73
3,824,766 7/1974 Valentine et al. ...................... 55/73

Primary Examiner—Bernard Nozick
Attorney, Agent, or Firm—Ralph M. Watson

[57] ABSTRACT

A method is disclosed for removing acidic gaseous components from natural gases, this method comprising an initial desulfurization stage employing a selective solvent, then removing carbon dioxide by low temperature distillation, the carbon dioxide providing the cooling effect required for such a condensation, recovering the solvent, absorbing the residual carbon dioxide with the regenerated solvent and recycling the CO$_2$-laden solvent to the desulfurization stage.

8 Claims, 1 Drawing Figure

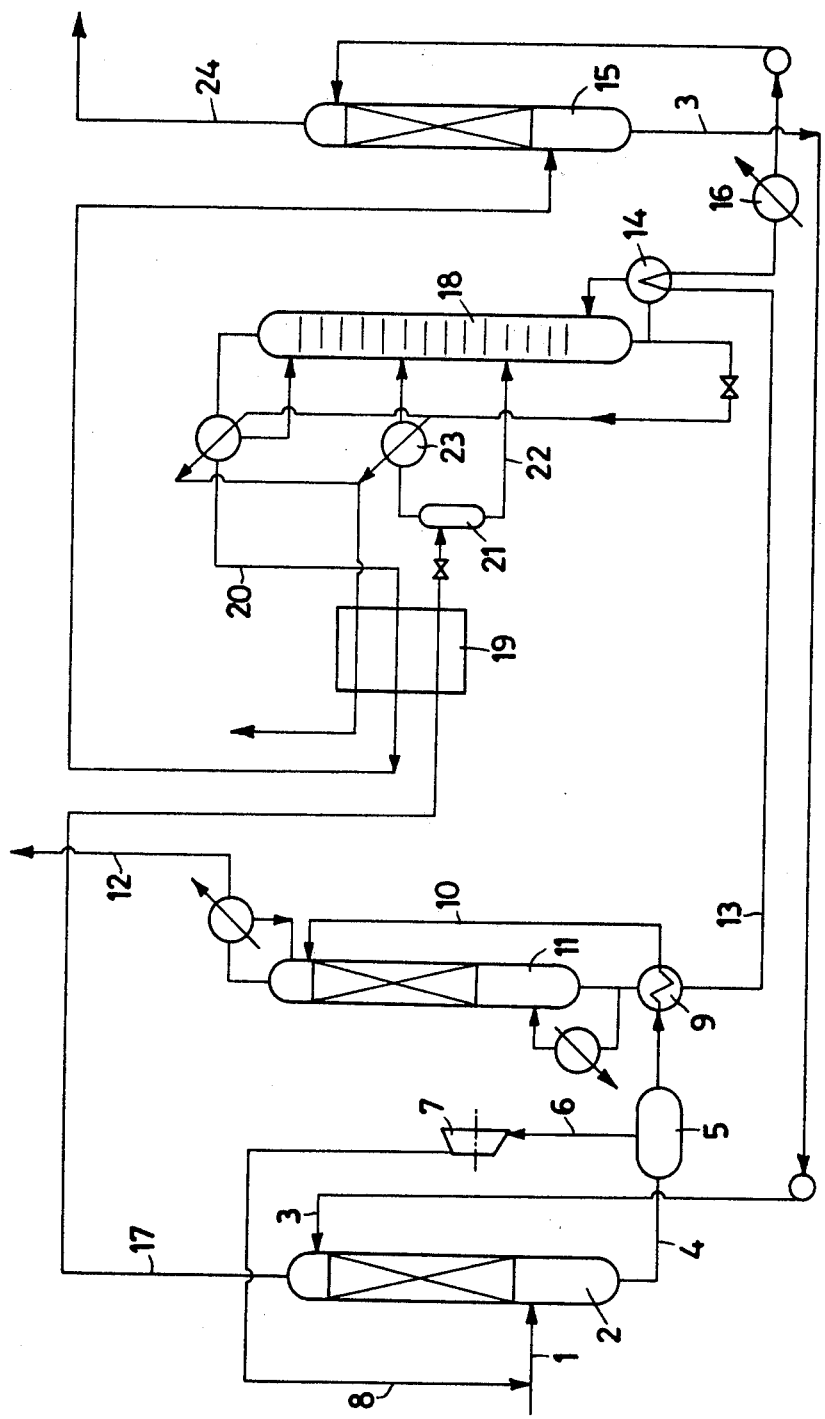

METHOD FOR THE PURIFICATION OF NATURAL GAS HAVING A HIGH CONTENTS OF ACIDIC GASES

This invention relates to a method for the purification of natural gas having a high content of acidic gases.

The natrual gas often contains considerable amounts of acidic gases, such as, essentially, $CO_2$ and $H_2S$.

The purification of natural gas from such acidic gases is necessary to permit the utilization of the natural gas and, at any rate, in order to reduce the volume of the useful gas to be shipped, thus reducing the shipping costs.

A composition of natural gas rich in acidic gases is the following:
- $CH_4$ 26.46% by volume
- $C_2H_6$ 0.44% by volume
- $C_nH_{2n+2}$ 0.27% by volume
- $N_2$ 0.49% by volume
- $CO_2$ 71.80% by volume
- $H_2S^2$ 0.54% by volume Other composition may obviously occur according to the natural deposit from which the natural gas is extracted.

In view of the fact that natural gas rich in acidic gases is often found in deposits which are offshore and far from the coast, it can easily be understood that the purification made necessary by the presence of such acidic gases requires that technical and ecological problems be solved, which are not negligible and are connected with the necessity of carrying out the purification operations on platforms so as to reduce the cost of the sealine to convey the natural gas to the coast: such a cost would grow in an excessive manner if one would convey the natural gas as such, due to the very high content of inerts.

The discharge in the atmosphere of enormous quantities of acidic gases could also create serious air pollution problems.

A method has now been found for the purification of natural gas having a high content of acidic gases, by which method the acidic gases in question are removed in a simple and cheap way while preventing pollution, the purification operation being susceptible of being easily carried out directly on an offshore platform.

The subject of the present invention is a method for the purification of natural gas, which essentially comprises the following steps:

(1) Subjecting the natural gas to desulfurization by causing the sulfurous compounds (from 0.1% to 5% by vol.), especially $H_2S$, contained in said gas, to be absorbed by a selective solvent for them, more particularly and preferably dimethyl-ether-dipolyglycol or propylene carbonate;

(2) removing major fraction of the $CO_2$, up to 20-30% of the $CO_2$ content of the desulfurized gas, by distillation at low temperatures (cryogenic stripping), the low temperatures which are required being obtained by evaporation at low pressure of the liquid $CO_2$ separated by such a distillation;

(3) regenerating the selective solvent by stripping it of the sulfurous compounds;

(4) utilizing the regenerated selective solvent to absorb the residual $CO_2$ still contained in the natural gas emerging from the cryogenic stripping stage, and (5) recycling the $CO_2$-containing selective solvent from stage 4 above to the absorption stage, 1, of the sulfurous compounds.

The temperatures as adopted in the desulfurization stage lie within the range from 20° C to 100° C whereas the pressure is generally in the range between 100 and 200 kilograms/sq. cm. absolute.

Low-temperature distillation is carried out at a columnhead temperature below −35° C and under a pressure in the range between 60 and 80 kgs./sq.cm absolute.

The regeneration of the selective solvent is generally carried out in a usual stripping column at a temperature in the range between 100° and 140° C and under a pressure of from 1 to 2 kgs/sq.cm absolute.

The final absorption of $CO_2$ (stage 4) is carried out at a temperature in the range between 3° C and 20° C and under a pressure of from 60 to 80 kgs.sq.cm. absolute.

The selective solvent which is recycled to stage 1 has a content of $CO_2$ equal to 9 to 16% of the total $CO_2$ contained in the natural gas (in the gaseous stage) at the start of the treatment according to the invention.

The invention will now be described in more detail with reference to the diagram shown in the accompanying drawing.

BRIEF DESCRIPTION OF THE DRAWING

The drawing is a schematic representation of apparatus adapted for use in carrying out the process which we have invented.

The natural gas rich in acidic gases is available under a pressure of 150 kgs/sq.cm and at room temperature and is fed, through 1, to the desulfurization column 2.

The natural gas has the composition as reported in the introductory part of this specification.

The absorption of $H_2S$ is carried out by using, as the solvent, dimethyl ether polyglycol fed via 3.

The natural gas is desulfurized down to 5 parts per million (ppm) of residual $H_2S$, whereas the $CO_2$ is absorbed only partially to a residual content of 69% by volume, approximately.

The solvent, and the substances dissolved thereby, is discharged through 4 and is subjected to a flashing operation under a pressure of about 75 to 80 kgs/sq.cm. A gaseous phase, 6, is thus separated in the collector 5, said phase being essentially rich in methane which, as compressed by the compressor 7, is recycled via the main 8 to the desulfurization column 2.

The liquid phase emerging from 5 is sent, upon preheating by the exhausted solvent at 9, through the duct 10 to the stripping column 11 wherein, at the head; there is obtained $H_2S$ at 12, which is then sent to burnout (conversion into $SO_2$ and $H_2O$) whereas, at the tail, the solvent 13 is obtained, which is sent for the absorption of the residual $CO_2$ in the absorption column 15, after having supplied the heat which is necessary for the cryogenic separation of the $CO_2$ at 14 and after having been cooled at 16 down to about 5° C.

The desulfurized gas which emerges from the column 2 is sent to the separation column 18 (pressure : 70 kgs/sq.cm) after having been cooled at 19 by the cold effluent which emerges from the top and the bottom of the column 18 aforesaid.

Prior to entering the column 18 and after having cooled as aforesaid, the gas 17 is caused isoenthalpically to be expanded to a pressure of about 70 kgs/sq.cm, thus separating in the separator 21 a liquid phase which, through the line 22, is sent to the low portion of the column 18, and a gaseous phase, which, after a further cooling at 23 by evaporating $CO_2$ (that which forms also a liquid phase) is conveyed to the intermediate portion of the column 18.

The liquid reflux to the head of the column 18 is obtained by condensing a portion of the vapors with evaporating $CO_2$, whereas liquid $CO_2$ is obtained as a bottom product and, by evaporation, supplies the refrigeration which is necessary for the refluxing and the condensation at 23 and at 19 as well.

The natural gas 20, which still contains $CO_2$ (20–30% by vol.) is sent to the absorption column 15 wherein the $CO_2$ is absorbed by the solvent 13 fed to the column 15 in counterflow relationship relative to the gas fed in the neighborhood of the column bottom. The purified gas is discharged through the duct 24 and is sent to the point of utilization through sealines or pipes. The $CO_2$-containing solvent is discharged from the bottom of the column 15, and via 3, is recycled to the column 2. Solvent make-up can obviously be effected at any point of the installation.

We claim:

1. The method of purifying natural gas having a high content of acidic gases, comprised of a sulfurous compound and $CO_2$, in a series of stages which include:

a first stage which comprises, desulfurizing the gas to be purified by feeding said gas and a selective solvent for said sulfurous compound to a desulfurization column so that the sulfurous compound is absorbed by said solvent, recovering the solvent and material absorbed thereby as bottom product from the desulfurization column and withdrawing desulfurized gas including natural gas and $CO_2$ from the head of the desulfurization column;

a second stage which comprises, regenerating the selective solvent recovered in the bottom product of said first stage by feeding said bottom product to a stripping column so that the sulfurous compound is stripped from the solvent therein, withdrawing said sulfurous product from the head of the stripping column, and recovering regenerated solvent from the stripping column as bottom product;

a third stage which comprises, removing the major fraction of the $CO_2$ from the desulfurized gas withdrawn from the desulfurization column in the first stage by feeding said desulfurized gas to a separation column so that said gas is subjected to a low temperature distillation whereby liquid $CO_2$ is separated from said desulfurized gas and wherein the necessary refrigeration is supplied by evaporating liquid $CO_2$ separated in said distillation, withdrawing liquid $CO_2$ from the separation column as bottom product, and recovering natural gas and the balance of the $CO_2$ from the head of the separation column;

a fourth stage which comprises, purifying the natural gas withdrawn from the head of the separation column in said third stage by feeding said head product from the third stage and said regenerated selective solvent recovered as bottom product in the second stage to an absorption column so that $CO_2$ in said third stage head product is absorbed by said regenerated selective solvent, recovering purified natural gas from the absorption column as head product, and withdrawing selective solvent and absorbed $OO_2$ from said absorption column as bottom product; and recycling said fourth stage bottom product to the first stage desulfurization column.

2. The method as claimed in claim 1, wherein the sulfurous compound is at a concentration of 0.1% to 5% by volume, and the $CO_2$ is at a concentration of at least 40% by volume.

3. The method as claimed in claim 1, wherein the major fraction of the $CO_2$ removed in the third stage is 20 to 30% by volume.

4. The method as claimed in claim 1, wherein the selective solvent is a member of the group consisting of dimethyl-ether-dipolyglycol and propylene carbonate.

5. The method as claimed in claim 1, wherein the low-temperature distillation in the third stage is carried out at a column-head temperature below $-35°$ C and the pressure is in the range between 60 and 80 kgs/sq. cm. absolute.

6. The method as claimed in claim 1, wherein the temperatures adopted in the first stage are in the range of from 20° C to 100° C and the pressures are in the range of from 100 to 200 kgs/sq.cm.

7. The method as claimed in claim 1, wherein the solvent stripping in the second stage is carried out at a temperature in the range of from 100° C to 140° C, and at a pressure in the range of from 1 to 2 kgs/sq.cm.

8. The method as claimed in claim 1, wherein the absorption of $CO_2$ in the fourth stage is carried out at a temperature in the range of from 3° C to 20° C and under a pressure in the range of from 60 to 80 kgs/sq.cm. absolute.

* * * * *

UNITED STATES PATENT AND TRADEMARK OFFICE
CERTIFICATE OF CORRECTION

PATENT NO. : 4,097,250
DATED : June 27, 1978
INVENTOR(S) : Giorgio Pagani, et al It is certified that error appears in the above–identified patent and that said Letters Patent are hereby corrected as shown below:

Col. 1, line 21, Correct "$H_2S^2$" to read --$H_2S$--.

Col. 4, line 16, Correct "$OO_2$" to read --$CO_2$--.

Signed and Sealed this

Fifth Day of June 1979

[SEAL]

Attest:

RUTH C. MASON
Attesting Officer

DONALD W. BANNER
Commissioner of Patents and Trademarks